United States Patent
Halkes et al.

(10) Patent No.: US 6,288,249 B1
(45) Date of Patent: Sep. 11, 2001

(54) VITAMIN D ANALOGS AND METHODS OF PREPARING THESE COMPOUNDS

(75) Inventors: Sebastianus J. Halkes; Jan Paul Van De Velde; Silvia Kanzler; Wolfgang Reischl, all of Weesp (NL)

(73) Assignee: Kingdom of the Netherlands (NL)

( * ) Notice: Subject to any disclaimer, the term of this patent is extended or adjusted under 35 U.S.C. 154(b) by 0 days.

(21) Appl. No.: 09/180,136

(22) PCT Filed: May 2, 1997

(86) PCT No.: PCT/EP97/02429
§ 371 Date: Jun. 16, 1999
§ 102(e) Date: Jun. 16, 1999

(87) PCT Pub. No.: WO97/42152
PCT Pub. Date: Nov. 13, 1997

(30) Foreign Application Priority Data

May 2, 1996 (EP) .................................................. 96201213

(51) Int. Cl.⁷ ........................ C07C 401/00; A61K 31/593
(52) U.S. Cl. ........................... 552/653; 552/653; 514/167
(58) Field of Search ............................... 552/653; 514/167

(56) References Cited

PUBLICATIONS

Carter et al. (Chemotherapy of cancer, pp. 364–365; second edition, John Wiley and sons, New york, 1981, appendix C).*
Posner et al., "1α,25–Dihydroxyvitamin D₃ Analogs Featuring Aromatic and Heteroaromatic Rings: Design, Synthesis, and Preliminary Biological Testing", J. Med. Chem., 38(22):4529–4537 (1995).
Chau, "Synthetic Studies on Vitamin D₃ Analogues: The Synthesis of 8–p–(Hydroxymethyl)–Phenyl–Des–A, B–Cholest–8(9)+8(14)ene," J. Chinese Chem. Soc., 28(1):29–33 (1981).

* cited by examiner

Primary Examiner—Sabiha Qazi
(74) Attorney, Agent, or Firm—Finnegan, Henderson, Farabow, Garrett & Dunner, L.L.P.

(57) ABSTRACT

The invention relates to vitamin D analogs of general formula (I) wherein: $R_1$ is a hydrogen atom or a substituent selected from the group consisting of hydroxy, $CH_2OH$, $CH_2CH_2OH$, $CH_2CH_2CH_2OH$, $OCH_3$, $OCH_2OH$, $OCH_2CH_2OH$ and $OCH_2CH_2CH_2OH$; $R_2$ is a hydrogen atom or a substituent selected from the group consisting of $OCH_3$, $OCH_2OH$, $CH_m(CH_2OH)_n(CH_2CH_2OH)_p$, $(CH_2)_qOH$ and $O(CH_2)_rOH$; wherein: m is 0 or 1, p, q and n are 0–3, r is 1–3 and m+n+p=3; with the proviso that $R_1$ and/or $R_2$ contain at least one OH group; $R_3$ is a straight or branched, saturated or unsaturated aliphatic hydrocarbon of 6–13 C atoms which may be substituted with one or more substituents from the group hydroxy or fluoro. The invention further relates to methods of preparing these compounds, a pharmaceutical composition containing these compounds and to their use in pharmacotherapy and cosmetics.

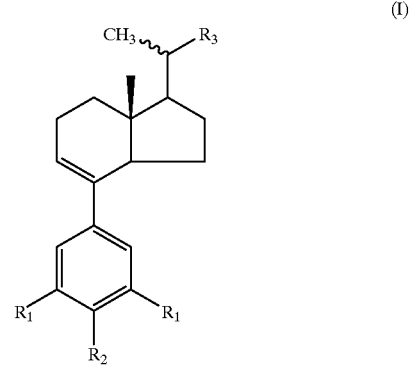

(I)

9 Claims, No Drawings

VITAMIN D ANALOGS AND METHODS OF PREPARING THESE COMPOUNDS

This application is a 371 of PCT/EP97/02429 filed May 2, 1997.

The invention relates to new vitamin D analogs, to methods of preparing these compounds and to their use in pharmacotherapy and cosmetics.

It is generally known, that vitamin-D compounds or vitamin-D related compounds ("vitamin-D analogs") have a strong biological activity and may be used in all those cases in which problems with the calcium and bone metabolism play a part. A few years ago it was found that various active vitamin-D compounds and analogs also have other pharmacotherapeutic activities and may be used successfully, for example, for the treatment of certain skin and bone diseases, for cosmetic applications and for treating diseases which are related to cell differentiation, cell proliferation or imbalance in the immune system, including diabetes mellitus, hypertension and inflammatory diseases such as rheumatoid arthritis and asthma. In addition, these compounds may be used in various veterinary applications, and for diagnostic purposes.

Further it is known from J. Med. Chem. 38 (1995), 4529–4537 that 1 α, 25-dihydroxy vitamin $D_3$ analogs of the formula

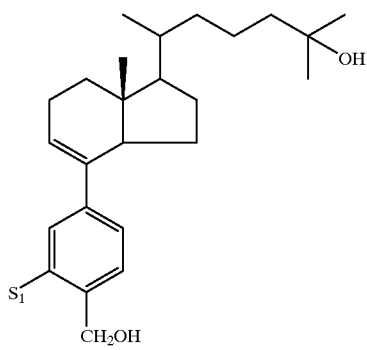

wherein $S_1$ is OH, $HOCH_2$— or $HOCH_2CH_2$ have very low affinities, i.e. no more than $10^{-3}$ the affinity of calcitriol, for the calf thymus vitamin D receptor, and considerable antiproliferative activities in murine keratinocytes.

Surprisingly it has now been found that a group of new vitamin D analogs has an activity of up to 6 times that of calcitriol, i.e. is much more active than the above mentioned known analogs, in the same test (affinity for the calf thymus vitamin D receptor).

The present invention relates to compounds of the general formula

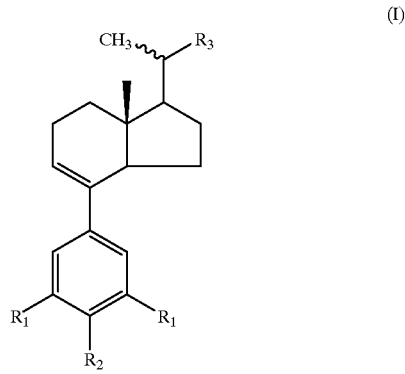

wherein
$R_1$ is a hydrogen atom or a substituent selected from the group consisting of $CH_2OH$, $CH_2CH_2OH$, $CH_2CH_2CH_2OH$, $OCH_3$, $OCH_2OH$, $OCH_2CH_2OH$ and $OCH_2CH_2CH_2OH$;

$R_2$ is a hydrogen atom or a substituent selected from the group consisting of $OCH_3$, $OCH_2OH$, $CH_m(CH_2OH)_n$ $(CH_2CH_2OH)_p$, $(CH_2)_qOH$ and $O(CH_2)_rOH$;
wherein:
m is 0 or 1, p, q and n are 0–3, r is 1–3 and m+n+p=3;
with the proviso that $R_1$ and/or $R_2$ contain at least one OH group;

$R_3$ is a straight or branched, saturated or unsaturated aliphatic hydrocarbon of 6–13 C atoms which may be substituted with one or more substituents from the group hydroxy or fluoro.

The above new vitamin D analogs of the invention, presented by the general formula I, are valuable substances. The biological results, as illustrated in the Examples, indicate that these compounds are promising as biologically active substances and may be used in all above-mentioned pharmacotherapeutic indications, more in particular for the treatment of osteoporosis, renal osteodystrophy, osteomalacia, skin disorders such as psoriasis (and other hyperproliferative skin diseases), eczema and dermatitis, myopathy, leukaemia, breast and colon cancer, osteosarcomas, squamous cell carcinomas, melanoma, certain immunological disorders, and transplant rejections.

Furthermore, the new vitamin D analogs of the invention may be used for wound healing and may be incorporated in cosmetic compositions, such as creams, lotions, ointments and the like, in order to preserve, condition and/or protect the skin and to improve various skin conditions, such as wrinkles, dry skin, skin slackness and insufficient sebum secretion. The new vitamin D analogs may also be used for diagnostic purposes.

Preferred compounds of the general formula (I) are the compounds wherein $R_3$ is the group —$(CH_2)_3$—$C(CH_3)_2OH$.

Especially preferred are the compounds of formula (I) wherein $R_3$ is the group —$(CH_2)_3$—$C(CH_3)_2OH$ and wherein:
a) $R_1$ is a hydrogen atom and $R_2$ represents $CH_2CH_2OH$, $CH_2CH_2CH_2OH$, $CH(CH_2CH_2OH)_2$, $C(CH_2CH_2OH)_3$ or $C(CH_2CH_2OH)_2CH_2OH$; or b) $R_1$ is OH, $CH_2OH$ or $(CH_2)_2OH$ and $R_2$ represents hydrogen, OH, $OCH_3$, or $O(CH_2)_rOH$, wherein r has the value 1 to 3.

Most particularly preferred are the compounds of formula (I) wherein $R_3$ is the group —$(CH_2)_3$—$C(CH_3)_2OH$ and wherein:

$R_1$ is hydroxy, $CH_2OH$ and $CH_2CH_2OH$ and $R_2$ represents hydrogen, $CH_2OH$ or $CH_2CH_2OH$.

It is a special merit of the present invention that the above new vitamin D analogs can easily be prepared from readily available starting materials.

Consequently, the invention also relates to a method of preparing a vitamin D analog of the general formula I, as defined above, which method is characterized in that a compound of the general formula (II)

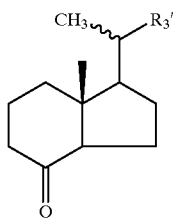

wherein:

$R_3'$ is a straight or branched, saturated or unsaturated aliphatic hydrocarbon of 6–13 C-atoms which may be substituted with one or more substituents from the group protected hydroxy or fluoro, is reacted with an organometallic compound of the general formula (III)

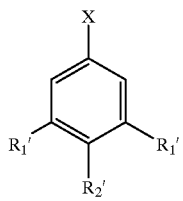

$R_1'$ and $R_2'$ are the hydroxy protected analogs of $R_1$ and $R_2$ defined above, X is Li, MgCl, MgBr or MgI, to yield a compound of the general formula (Ia)

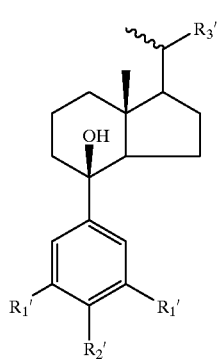

followed by dehydration and deprotection of the hydroxy group(s).

The compounds having formula I can also be obtained by reacting a compound of the general formula (IV)

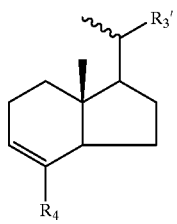

wherein $R_3'$ has the meaning given above, and $R_4$ is a protected hydroxy group, with a compound of the general formula (IIIa)

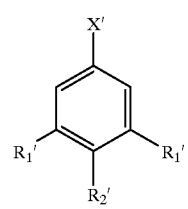

wherein X' is halogen, preferably Br, and $R_1'$ and $R_2'$ have the above given meanings, under the influence of an alkyl lithium compound, a zinc halogenide, preferably $ZnCl_2$, and a transmetallation catalyst, followed by deprotection of the hydroxy group(s). An example of a transmetallation catalyst is tris-(dibenzylidene-acetone)-dipalladium(0).

The enolic hydroxy group of enolized compound IV is preferably derivatized by a reaction with N-aryltriflimide to produce a triflate.

To improve the applicability of the new vitamin D analogs of the invention for the above-described pharmacotherapeutic indications, the compounds are usually processed to pharmaceutical compositions, comprising an effective amount of said vitamin D analog as the active ingredient in addition to a pharmaceutically acceptable carrier and/or at least one pharmaceutically acceptable auxiliary substance. Such a composition may be delivered in a dosage unit form for oral, topical (dermal) or parenteral administration, comprising approx. 0.1 µg to approx. 0.1 mg active ingredient per dosage unit. A composition for diagnostic purposes may comprise, in addition to the vitamin D analog of the present invention, a compatible, non-toxic carrier and/or at least one auxiliary substance.

A cosmetical composition may comprise, in addition to an effective amount (in the range of approx. 0.1 µg to. approx. 0.1 mg per dosage unit in a dosage unit form) of the vitamin D analog of the present invention, a cosmetically acceptable, non-toxic carrier and/or at least one auxiliary substance.

Finally the invention relates to a method for the treatment and prophylaxis of a number of disease states including autoiummune diseases (including diabetes mellitus), acne, alopecia, skin aging (including photo-aging), imbalance in the immune system, inflammatory diseases such as rheumatoid arthritis and asthma, as well as diseases related to abnormal cell differentiation and/or proliferation, in a warmblooded living being, comprising administering to said being or treating said being with a pharmaceutical composition as defined above in a quantity effective for the intended purpose. Examples of such diseases are psoriasis and other hyperproliferative skin diseases.

The present invention also relates to the use of the above pharmaceutical compositions for the treatment of solid, skin and blood cancers, in particular of blood cancers such as leukaemia, of breast and colon cancer, and of skin cancers such as melanoma and squamous cell carcinoma.

The above-defined cosmetical compositions, in particular selected from the group consisting of creams, lotions, ointments, liposomes and gels, can be used for the treatment and prevention of a number of skin disorders, such as inadequate skin firmness or texture, insufficient skin hydration, wrinkles and insufficient sebum secretion.

The invention will now be described in greater detail with reference to the following specific Examples.

The following abbreviations are used in the examples:
THF=tetrahydrofuran
TBDMS=tert.-butyl dimethyl silyl
DMF=N,N-dimethylformamide
$Pd_2dba_3$=tris-(dibenzylideneacetone)dipalladium (0)

Examples

The TBDMS protected compound (IIIa) wherein X'=Br is dissolved in dry THF, cooled to −78° C. and treated with 2 eq. of tert. $C_4H_9Li$. After 30 minutes a solution of 1 eq. $ZnCl_2$ in dry THF is added and stirring is continued another 15 minutes. A solution of 1.1 eq. of a compound IV wherein $R_4$ is $CF_3SO_3$—, 5 mol % of the catalyst $Pd_2dba_3$ and 10 mol % of $As_3P$ in dry DMF is introduced by means of double ended needle technique. The mixture is stirred at room temperature until the catalyst has completely dissolved. The progress of the reaction is monitored by thin-layer-chromatography. The reaction mixture is worked up by flash-chromatography. Complete deprotection of the hydroxy groups is carried out by treatment of the obtained product with an ion exchange resin, such as DOWEX-50 W, in methanol.

The following compounds of formula (I) have been prepared in this manner:

| Comp. No. | $R_1$ | $R_2$ | $R_3$ | Yield (%) |
|---|---|---|---|---|
| 1 | $CH_2CH_2OH$ | H | $(CH_2)_3$—$C(CH_3)_2OH$ | 79 |
| 2 | OH | H | $(CH_2)_3$—$C(CH_3)_2OH$ | 51 |
| 3 | H | $CH_2OH$ | $(CH_2)_3$—$C(CH_3)_2OH$ | 82 |
| 4 | H | $CH_2CH_2OH$ | $(CH_2)_3$—$C(CH_3)_2OH$ | 88 |
| 5 | $CH_2OH$ | H | $(CH_2)_3$—$C(CH_3)_2OH$ | 57 |

$^1$H-NMR data ($CDCl_3,\delta$) of compounds no.s 1–5:

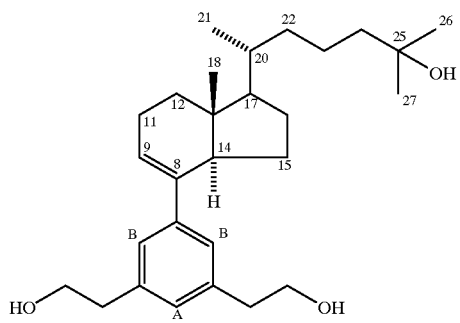

No. 1

400 mHz $^1$H-NMR ($CDCl_3,\delta$): 0.76 ($C_{18}H_3$; 3H; s); 1.00 ($C_{21}H_3$; 3H, d); 1.22 ($C_{26,27}H_3$, 6H; S); 2.27 ($C_{11}H_2$, 2H, b); 2.58 ($C_{14}H$; 1 H, b); 2.83 (Φ-$CH_2$ —C, 2x; 4H, t); 3.85 (2x Φ-C—$CH_2$—O, 4H, t); 5.64 ($C_9H$; 1H, b); 6.92 (A, 1H, s); 6.93 (B; 2H, s).

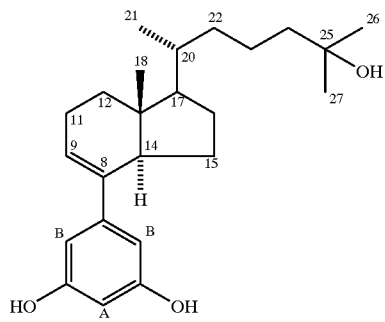

No. 2

400 mHz $^1$H-NMR ($CDCl_3$, δ): 0.73 $C_{18}H_3$; 3H,s); 0.99 ($C_{21}H_3$, 3H, d); 1.19 ($C_{26,27}H_3$; 6H,s); 2.23 ($C_{11}H_2$, 2H, b); 2.48 ($C_{14}H$, 1H, b); 5.58 ($C_9H$, 1H, b); 6.16 (B, 2H, s); 6.20 (A, 1H, s); 8.53 (2xΦ-OH, 2H, s).

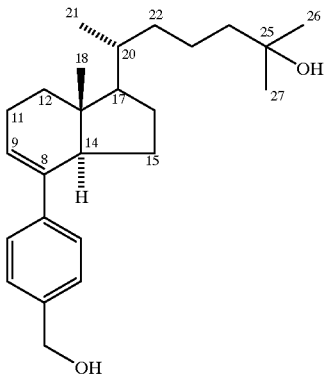

No. 3

400 mHz $^1$H-NMR ($CDCl_3$, δ): 0.77 ($C_{18}H_3$; 3H, s); 1.00 ($C_{21}H_3$, 3H, d); 1.21 ($C_{26,27}H_3$; 6H, s); 2.58 ($C_{14}H$, 1H, b); 4.65 (Φ-$CH_2$—O, 2H, s); 5.63 ($C_9H$; 1H, b); 7.18 (Φ-H, 2H, t); 7.26 (Φ-H, 2H, b).

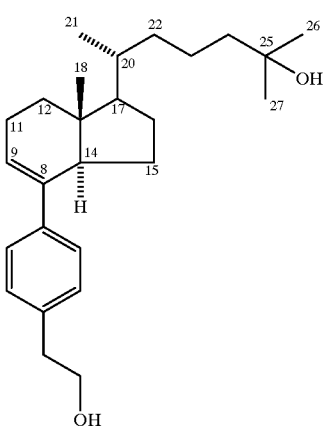

No. 4

400 mHz $^1$H-NMR ($CDCl_3$, δ): 0.76 ($C_{18}H_3$, 3H, s); 1.00 ($C_{21}H_3$; 3H, d); 1.22 ($C_{26,27}H_3$; 6H, s); 2.60 ($C_{14}H$, 1H, b); 2.84 (Φ-$CH_2$—C, 2H, t); 3.85 (Φ-C—$CH_2$—O, 2H, t); 5.62 ($C_9H$, 1 H, b); 7.14 (Φ-H, 4H, b).

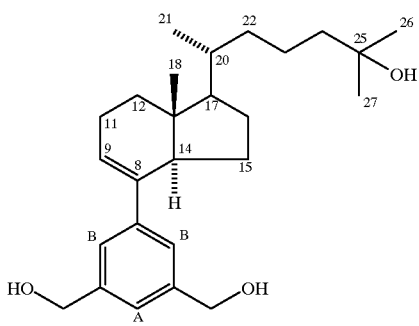

No. 5

400 mHz $^1$H-NMR (CDCl$_3$, δ): 0.76 (C$_{18}$H$_3$, 3H, s); 1.00 (C$_{21}$H$_3$, 3H, d); 1.22 (C$_{26,27}$H$_3$, 6H, s); 2.59 (C$_{14}$H, 1H, b); 4.64 (2x Φ-CH$_2$—O, 4H, s); 5.65 (C$_9$H; 1H, b); 7.11 (2x B; 2H, s); 7.18 (A, 1H; s).

Affinity Towards the Intracellular Vitamin D Receptor

The aromatic vitamin D analogs were dissolved in ethanol in concentrations ranging from $10^{-14}$ to $10^{-6}$ M. The affinity towards the calf thymus intracellular vitamin D receptor (VDR) was determined in a biological in vitro assay and compared to that of calcitriol. In this assay, labelled $^3$H-calcitriol, which is specifically bound to the VDR, is replaced by the aromatic vitamin D analog. Compounds 5 and 3 have even higher affinities (resp. 6 and 3 times) than calcitriol itself towards the highly selective VDR. Also analogs 4 and 1 demonstrate high VDR affinities. A high VDR affinity is indicative for biologically active substances.

The compounds with the highest affinities were therefore further tested in vitro.

Affinity to Human Blood Vitamin D Binding Protein

Vitamin D binding protein (DBP) is the specific carrier for vitamin D and its metabolites in blood. The biological activity of vitamin D analogs depends on their binding to DBP. Strong binders will have reduced access to the VDR. Weak binders are rapidly metabolized, which is a favourable aspect in topical application.

DBP is purified from total human serum. In the assay, DBP is incubated with $^3$H-calcitriol and calcitriol or one of the aromatic vitamin D analogs. To this purpose, the vitamin D analogs are dissolved in ethanol in concentrations ranging from $10^{-11}$ to $2.5 \times 10^{-6}$.

The percentage bound/unbound $^3$H-calcitriol is then calculated. Compounds 5, 4 and 3 (in order of binding) are relatively good binders, binding a factor 2–10 less than calcitriol itself. These binding capacities show that the compounds might have systemic actions, i.e. they might be active when administered orally or given by injection.

What is claimed is:

1. A vitamin D compound of formula (I):

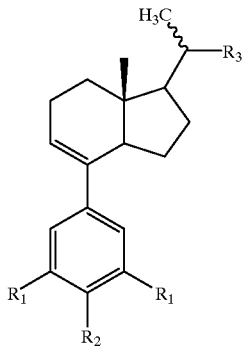

(I)

wherein:

R$_1$ is a hydrogen atom or a substituent selected from the group consisting of OH, CH$_2$OH, CH$_2$CH$_2$OH, CH$_2$CH$_2$CH$_2$OH, OCH$_3$, OCH$_2$OH, OCH$_2$CH$_2$OH and OCH$_2$CH$_2$CH$_2$OH;

R$_2$ is a hydrogen atom or a substituent selected from the group consisting of OCH$_3$, OCH$_2$OH, CH$_m$(CH$_2$OH)$_n$ (CH$_2$CH$_2$OH)$_p$, (CH$_2$)$_q$OH and O(CH$_2$)$_r$OH;

wherein:

m is 0 or 1; p, q, and n are independently 0, 1, 2 or 3;
r is 1, 2 or 3;
and m+n+p=3;

with the proviso that at least one of R$_1$ and R$_2$ contains at least one OH group and;

with the proviso that both R$_1$ substituents are the same;

R$_3$ is a straight or branched, saturated or unsaturated aliphatic hydrocarbon having from 6 to 13 carbon atoms which may be substituted with one or more substituents selected from the group consisting of hydroxy and fluoro.

2. The compound of formula (I) as claimed in claim 1, wherein R$_3$ is —(CH$_2$)$_3$—C(CH$_3$)$_2$OH.

3. The compound of formula (I) as claimed in claim 2, wherein:

(a) R$_1$ is a hydrogen atom and R$_2$ represents CH$_2$CH$_2$OH, CH$_2$CH$_2$CH$_2$OH, CH(CH$_2$CH$_2$OH)$_2$, C(CH$_2$CH$_2$OH)$_3$ or C(CH$_2$CH$_2$OH)$_2$CH$_2$OH; or (b) R$_1$ is OH, CH$_2$OH or (CH$_2$)$_2$OH and R$_2$ represents hydrogen, OH, OCH$_3$, or O(CH$_2$)$_r$OH, wherein r has the value 1, 2 or 3.

4. The compound of formula (I) as claimed in claim 1, wherein R$_1$ is hydroxy, CH$_2$OH or CH$_2$CH$_2$OH, and R$_2$ represents hydrogen, CH$_2$OH or CH$_2$CH$_2$OH.

5. A method for preparing the vitamin D compound claimed in claim 1, which method comprises reacting, under the influence of an alkyl lithium compound, a zinc halogenide, and a transmetallation catalyst, a compound of formula (IV):

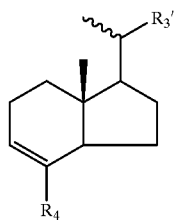

(IV)

wherein:
R$_3$' is a straight or branched, saturated or unsaturated aliphatic hydrocarbon having from 6 to 13 carbon atoms which may be substituted with one or more substituents selected from the group consisting of protected hydroxy and fluoro; and R$_4$ is a protected hydroxy group;
with a compound of formula (IIIa):

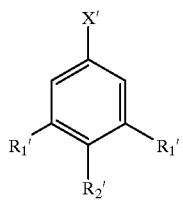

(IIIa)

wherein:

X' is halogen; and

R$_1$' and R$_2$' are the hydroxy protected forms of groups R$_1$ and R$_2$ defined in claim 1; and subsequently deprotecting the hydroxy groups of R$_1$' and R$_2$'.

6. The method of claim 5, wherein X' is bromine.

7. The method of claim 5, wherein the zinc halogenide is zinc chloride.

8. A pharmaceutical composition comprising:

a pharmaceutically effective amount of at least one compound of formula (I) defined according to claim 1, and at least one pharmaceutically acceptable carrier, at least one pharmaceutically acceptable auxiliary substance, or a combination thereof.

9. A method for preparing the pharmaceutical composition claimed in claim 8, wherein the method comprises combining said pharmaceutically effective amount of at least one compound of formula (I) with said at least one pharmaceutically acceptable carrier, said at least one pharmaceutically acceptable auxiliary substance, or a combination thereof.

\* \* \* \* \*